United States Patent
Dave

(10) Patent No.: US 6,849,303 B2
(45) Date of Patent: Feb. 1, 2005

(54) METHOD FOR ELECTROSTATICALLY COATING A FIBER SUBSTRATE

(76) Inventor: Vipul Bhupendra Dave, 20 Francis Dr., Belle Mead, NJ (US) 08502

(*) Notice: Subject to any disclaimer, the term of this patent is extended or adjusted under 35 U.S.C. 154(b) by 0 days.

(21) Appl. No.: 10/287,198

(22) Filed: Nov. 4, 2002

(65) Prior Publication Data

US 2003/0134052 A1 Jul. 17, 2003

Related U.S. Application Data

(63) Continuation of application No. 09/607,031, filed on Jun. 29, 2000, now abandoned.

(51) Int. Cl.$^7$ ................................................ B05D 1/22
(52) U.S. Cl. ....................... 427/459; 427/461; 427/482; 427/485
(58) Field of Search ................................ 427/459, 461, 427/482, 485, 475, 229; 132/321, 329

(56) References Cited

U.S. PATENT DOCUMENTS

| | | | | |
|---|---|---|---|---|
| 3,800,812 A | * | 4/1974 | Jaffe | 132/321 |
| 3,830,246 A | * | 8/1974 | Gillings | 132/321 |
| 3,919,437 A | * | 11/1975 | Brown et al. | |
| 5,042,122 A | | 8/1991 | Iyer et al. | |
| 5,094,883 A | * | 3/1992 | Muzzy et al. | 427/185 |
| 5,102,690 A | | 4/1992 | Iyer et al. | |
| 5,220,932 A | * | 6/1993 | Blass | |
| 5,312,642 A | * | 5/1994 | Chesterfield et al. | |
| 5,755,243 A | * | 5/1998 | Roberts et al. | 132/321 |
| 6,475,553 B2 | | 11/2002 | Guay et al. | |
| 2002/0083955 A1 | * | 7/2002 | McDevitt et al. | 132/321 |

OTHER PUBLICATIONS

Helmut Bauch, Influence of Chemophysical Powder Properties on Charging and Applying Processes by Electrostatic Powder Coating, University of Transport and Communications, Germany, pp. 344–347.

Robert M. Baucom et al. "LaRC Powder Prepreg System", NASA Langley Research Center, SAMPE Quarterly, pp. 14–19.

J. Muzzy et al. Electrostatic Prepregging of Thermoplastic Matrices, SAMPE Journal, vol. 25, No. 5, Sep./Oct. 1989.

R.A. Buchner et al. Parametric Statistical Analysis of Electrostatic Powder Prepregging, Journal of Advanced Materials, Jul. 1994, pp. 44–50.

A. Miller et al. Impregnation Techniques for Thermoplastic Matrix Composites, Polymers & Polymer Composites, vol. 4, No. 7, 1996, pp. 459–481.

A. L. Ogden et al. The Development of an Alternative Thermoplastic Powder Prepregging Technique, Journal of Thermplastic Composite Materials, vol. 5, Jan. 1992, pp. 14–31.

Karthik Ramani et al. an Electrostatic Powder Spray Process for Manufacturing Thermoplastic Composites, Polymer Composites, Dec. 1995, vol. 16, No. 6, pp. 459–469.

Martin Rhodes, Gas Fluidization, Technology, pp. 121–123.

S. Sampuran–Singh et al. A Parametric Study of Electrostatic Powder Coating, Journal of Electrostatics, 4 (1978) 325–334.

S. Wu, Electrostatic Charging and Deposition of Powder Coatings, Polym.–Plast. Technol. Eng., 7(2), 119–220 (1976).

\* cited by examiner

Primary Examiner—Fred J. Parker

(57) ABSTRACT

The use of electrostatic impregnation to load materials such as binders and flavors onto substrates such as fibers and medical devices is disclosed. Substrates loaded with materials such as binders and flavors, wherein the materials are loaded on the substrates via electrostatic impregnation are also disclosed.

6 Claims, 1 Drawing Sheet

Figure 1:
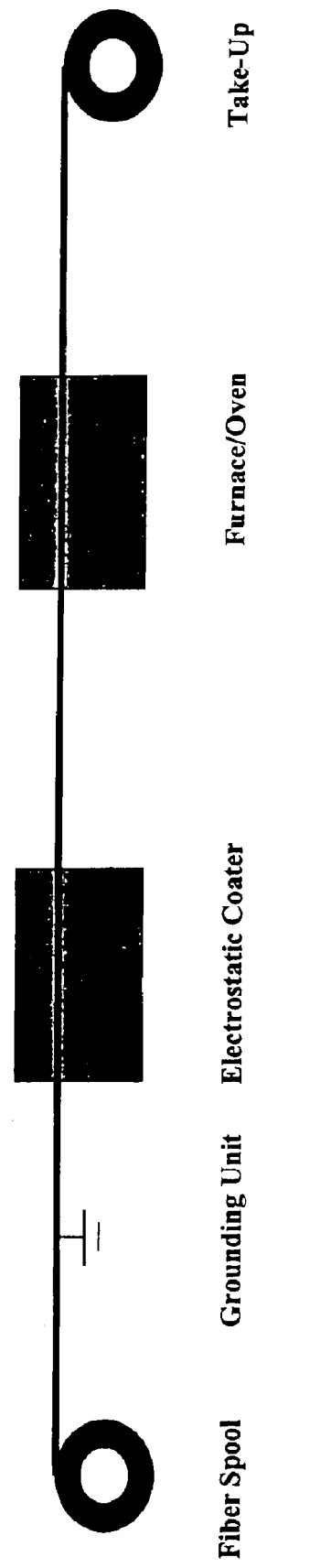

Fiber Spool    Grounding Unit    Electrostatic Coater    Furnace/Oven    Take-Up

METHOD FOR ELECTROSTATICALLY COATING A FIBER SUBSTRATE

This application is a continuation of U.S. Ser. No. 09/607,031, filed Jun. 29, 2000 now abandoned.

The present invention relates to the use of electrostatic impregnation to load materials such as binders and flavors onto substrates such as fibers and medical devices made from ceramics, metal alloys, and polymers. The invention also relates to substrates loaded with materials such as binders and flavors, wherein the materials are loaded into or on the substrates via electrostatic impregnation.

Many substrates are coated with materials such as polymers, polymeric binders, wax binders, flavors, and the like. For example, medical devices, such as stents, which are used in the human body, are frequently made of metal alloys. The stents require coating with a polymer or wax before use in the body. Another example of a substrate that is typically coated, e.g., with a polymer, a wax or the like, is dental floss.

Currently, dental floss has three main consumer needs that are not achieved in all products. These needs are (i) prevention/minimization of fraying and shredding during use, (ii) easy insertion and sliding between tight teeth and (iii) gentleness to the gums. As used herein, "fraying" means the separation of fibers by the stress placed on the floss during use between the teeth. As used herein, "shredding" means the breaking of fibers by the stress placed on the floss during use between the teeth. The minimization of fraying and shredding of dental floss is extremely important, as fraying and shredding are the most frequently encountered consumer complaints about floss.

Traditionally, floss consists of continuous fibers coated with wax containing additives such as flavors, sweeteners and one or more active ingredients. The microcrystalline wax that is currently used holds the fibers together and facilitates the repetitive sliding motion of floss between teeth. Shear forces applied to floss during use lead to fraying and shredding of the fibers. Such fraying and shredding occur primarily because the stresses applied to the floss during use tend to exceed the cohesive forces of wax that help bond the fibers together.

There are two possible routes that can be adopted in order to overcome the floss shredding problem. These include making the floss from a monofilament of suitable size or a "psuedo-monofilament", i.e., bonding the plurality of filaments in a multifilament structure such that they are adhered together and function like a monofilament. Pseudo-monofilament dental flosses are very similar to fiber-reinforced composites, in which fibers are impregnated with polymer matrices, which can be thermoset or thermoplastic in nature.

Composites are matrixes, e.g., a matrix comprising a polymeric resin, that are reinforced with another material. For fiber composites, the reinforcing material is fibers. The composite may be used as a dental floss. A study of the available composite manufacturing techniques leads to the understanding that two important stages exist. In stage one, the fibers and binder polymers are brought into intimate contact. In stage two, heat and pressure are applied in order to impregnate and consolidate the components. Stage one is crucial, as it brings the matrix polymer and fiber in closer proximity to each other, thereby minimizing the flow length required during consolidation. This first stage is what makes processing techniques used for thermoplastic composites different from thermoset composites, due to their higher viscosities.

It is known to overcome this problem by trying to reduce the viscosity of the resin in order to achieve rapid impregnation of the reinforcing fibers. This is called a pre-impregnation processes.

Solvent or solution impregnation has been used primarily where the high viscosity of the matrix material is reduced using solvents or plasticizers by dissolving the polymer in the solvent. The fibers are then made to pass through a dip bath filled with the solution of matrix material. The fibers are coated and the coated fibers are then passed through a series of dryers in order to remove the solvent, thereby providing the finished composite. The biggest disadvantage of such a process is environmental concerns regarding use of the solvent. In addition, manufacturing speed is very low, and thus manufacturing costs are increased.

The process described above requires dissolving a coating material in a solvent prior to coating a substrate. Dissolving the coating material may be undesirable, as there is an environmental concern over volatile organic compounds. Therefore, there is a need for a process of coating a substrate that does not require dissolving a coating in a solvent.

Powder impregnation is a more versatile process, as it will process both low and high viscosity resins as long as they can be obtained in the powder form, and the process is relatively simple.

Investigators at Georgia Tech have developed a system wherein glass fibers are spread using up to 8 Teflon* coated rollers after which the spread fibers have a powder deposited thereon using a deposition system developed by Electrostatic Technology Incorporated (ETI). In this system, powder particles are charged and are then electrostatically deposited onto the glass fiber. The above-mentioned rollers were found, however, to cause damage to the fiber and a transition was then made to a different fiber spreading technology known as pneumatic venturi spreading. This effort lead to the issuance of U.S. Pat. No. 5,094,883. In the patent, the importance of flexible fiber impregnation production was taught for applications such as braiding and weaving.

None of the dental floss patents of which the inventor is aware have applied a powder technology approach for coating the substrate fibers of the dental floss with polymers. There is a continuing need for a process of coating substrates such as fibers and medical devices which does not require dissolving a coating in a solvent.

The present invention provides a process including: providing a substrate; and electrostatically coating the substrate with at least one coating material. In another embodiment, the present invention provides a substrate coated by electrostatic impregnation. The invention utilizes electrostatic powder coating technology to coat a substrate with materials such as waxes; thermoplastic polymers; additives such as spray-dried flavors and sweeteners; active ingredients such as sodium fluoride; abrasives; etc. This method can be used for coating any substrate including, but not limited to films, non-wovens, monofilament fibers, multi-filament fibers, medical devices, hair, sutures, and metal devices as long as the coating materials are in a powder form. The preferred substrates are monofilament fibers, multi-filament fibers, and medical devices. The coated fibers may be useful in applications such as, but not limited to, dental tapes and dental floss. The medical devices may be made of ceramics, metal alloys, or polymers. The medical devices may be useful in applications such as, but not limited to, stents and polymer tubes such as catheters.

The approach for electrostatically coating floss adopted in the present invention is to prepare a pseudo-monofilament by using waxes or thermoplastic polymers to adhere the fibers to each other before coating the resulting pseudo-monofilament with a desired coating composition which may include, for example, waxes, thermoplastic polymers, flavors and other additives. Some of the advantages of using waxes or thermoplastic polymers as the coating materials are the ease of processability, toughness, durability, long shelf life, lack of cross-linking chemical reactions and relatively high manufacturing speed. The drawbacks, however, are very high melt viscosities (in the range of $10^4$ poise) which lead to challenges in the areas of total fiber wet-out, interface control and mass production.

In the present invention, wax or polymer powder impregnation has been chosen to accomplish the challenge of bringing the fiber and matrix into contact by using an electrostatic deposition chamber. The technique has the ability to support continuous production of fibrous substrates which can then be integrated into a consolidation line that can use techniques such as calendering, hot-gun heating, filament winding and hand lay-up to apply pressure and heat in order to produce the floss product. Once the fibers have been bonded together, wax and other additives can be applied to the bonded substrate.

The physics of charging polymeric particles is not always easy to comprehend and is far from being completely tied to the chemistry of the polymer powder. However, a considerable amount of research has been done in the area with regard to electrostatic spray guns in the painting and coating industry.

Powders acquire charge in two ways: tribocharging and corona charging. Corona charging results when particles receive a charge from electrically charged air. Tribocharging occurs when powder, during transportation from a reservoir to the spray gun or coater bed, undergoes frictional contact with an unsymmetrical surface. This unsymmetry could be due to velocity, temperature or chemical composition. The polarity and magnitude of the tribocharge depend on the nature of the powder, the travel velocity, and the nature of the contact tubing. Formulation chemistry of the polymer could also determine the nature, i.e., positive or negative, of the acquired charge. Usually the charging is higher at lower transportation rates and decreases as transportation rates increase. On the other hand, corona charging occurs in the region between the corona glow and the substrate. For particles beyond a certain size (>0.5 microns) field charging predominates. Below a size of 0.2 microns however, the charge diffuses through the air.

According to theory, the saturation charge per ball-shaped particle is directly proportional to the square of the particle radius and inversely proportional to its mass. The shape of the particle was found to not deviate in most cases from the ball-shape and so approximations made with regards to the spherical nature of the particle in theoretical calculations are still fairly accurate. In regard to the sign (i.e., positive or negative) and magnitude of the charge the electron affinity of the elements or functional groups bound to the carbon atoms and their stereometric arrangement in the macromolecule proves to be decisive.

A comparison shows that the increasing tendency to charge negatively moves in accordance with the increasing work function of the electron [poly methyl(methacrylate), polyethylene, poly (vinylchloride), poly (tetrafluoroethylene)], while materials with the lowest work functions tend to charge positively (e.g., polyamide). In spray gun applications, aerodynamic forces are responsible for transporting the powder towards the object and electrostatic forces are responsible once the powder is near the substrate in order to facilitate good wrapping of the coating around the fibers.

Suitable fibers to be used in the present invention include, but are not limited to, natural fibers such as cellulose, cellulosic fibers, and rayon; polyolefins such as polyethylene and polypropylene; polyesters such as polycaprolactone ("PCL"), poly(ethylene terephthalate) ("PET"), poly(butylene terephthalate) ("PBT"), and VECTRAN (Trademark of Hoechst-Celanese); polyamides such as nylon 6, nylon 11, nylon 12, and nylon 6,6; poly(ether-amides) such as, but not limited to, PEBAX 4033 SA and PEBAX 7233 SA (Trademark of Elf Atochem); poly(ether-esters) such as, but not limited to, HYTREL 4056 (Trademark of Dupont) and RITEFLEX (Trademark of Hoechst-Celanese); fluorinated polymers such as poly (vinylidine fluoride) and poly(tetrafluoroethylene); and combinations thereof, including bicomponent fibers, which may be core-sheath fibers. Texturized fibers may also be used.

The bicomponent fibers may have cross-sectional shapes such as round; trilobal; cross; and others known in the art. The core-sheath bicomponent fibers are typically made such that the sheath of the fibers utilizes a lower melting point polymer than the core polymer.

Suitable polymers for the core include polyamides such as, but not limited to, nylon 6, nylon 11, nylon 12, and nylon 6,6; polyesters such as, but not limited to, PET and PBT; poly(ether-amides) such as, but not limited to, PEBAX 4033 SA and PEBAX 7233 SA (Trademark of Elf Atochem); poly(ether-esters) such as, but not limited to, HYTREL 4056 (Trademark of Dupont) and RITEFLEX (Trademark of Hoechst-Celanese); polyolefins such as, but not limited to, polypropylene and polyethylene; and fluorinated polymers, such as, but not limited to, poly(vinylidene fluoride); and mixtures thereof. Nylon 6 and polypropylene are preferred.

Suitable polymers for the sheath include polyolefins such as, but not limited to, polyethylene ("PE") and polypropylene; polyesters such as, but not limited to, PCL; poly(ether-amides) such as, but not limited to, PEBAX 4033 SA and PEBAX 7233 SA (Trademark of Elf Atochem); poly(ether-esters) such as, but not limited to, HYTREL 4056 (Trademark of DuPont) and RITEFLEX (Trademark of Hoechst-Celanese); elastomers made from polyolefins, for example ENGAGE elastomers (Trademark of Dupont-Dow); poly(ether urethanes) such as, but not limited to, ESTANE poly(ether urethanes) (Trademark of BF Goodrich); poly(ester urethanes) such as, but not limited to, ESTANE poly(ester urethanes) (Trademark of BF Goodrich); KRATON polymers (Trademark of Shell Chemical Company) such as, but not limited to poly(styrene-ethylene/butylene-styrene); and poly(vinylidene fluoride) copolymers, such as, but not limited to, KYNARFLEX 2800, (Trademark of Elf Atochem). PEBAX polymers, polyethylene, and PCL are preferred.

The ratio of the two components of the core-sheath fibers can be varied. All ratios used herein are based on volume percents. The ratio may range from about 10 percent core and about 90 percent sheath to about 90 percent core and about 10 percent sheath, preferably from about 20 percent core and about 80 percent sheath to about 80 percent core and about 20 percent sheath, more preferably from about 30 percent core and about 70 percent sheath to about 70 percent core and about 30 percent sheath. The sheaths of the bicomponent fibers may be fused prior to electrostatic coating.

The substrates are electrostatically coated with at least one coating composition. Suitable first coatings to be used in the present invention include, but are not limited to, poly (ethylene oxide); poly(ethylene glycol); hydroxyethyl cellulose; hydroxypropyl cellulose; polyethylene; waxes such as microcrystalline wax; polyvinylidene fluoride and polycaprolactone.

Suitable second coatings to be used in the present invention include, but are not limited to, poly(ethylene oxide), poly(ethylene glycol), hydroxyethyl cellulose, hydroxypropyl cellulose, polyethylene, waxes such as microcrystalline wax, and polycaprolactone. The coatings may contain flavors, such as, but not limited to, natural and synthetic flavor oils, such as mint and cinnamon. The flavor oils may be used as is, or may be encapsulated in or supported on a carrier such as starch or modified starch.

The process of the invention may also be useful for orienting short bicomponent fibers perpendicular to the axis of a substrate, then fusing the short bicomponent fibers to the substrate. The length of the short bicomponent fibers may range from 1 mm to 5 mm. After the short bicomponent fibers are oriented onto the substrate by electrostatic impregnation, they are fused to the substrate by heat at a temperature appropriate to melt the outer surface of the bicomponent fiber.

Additional materials that may be included in the coatings include, but are not limited to, sweeteners such as bulk sweeteners, including sorbitol and mannitol, and intense sweeteners including aspartame and sodium saccharin, as taught by European Patent Application EP 919,208, hereby incorporated by reference for the disclosure relating to waxes and sweeteners; abrasives, such as silica; dentrifices; chemotherapeutic agents; cleaners; and whiteners. Examples of suitable additives are disclosed in U.S. Pat. No. 5,908,039, the disclosure of which is hereby incorporated by reference. Any of the foregoing materials may be used in encapsulated form.

The amount of wax, flavor, and other additives typically coated on fibers to make floss is known in the art. Typically, the coating composition is added at from 2 weight percent to 60 weight percent, based on the weight of the fibers.

Suitable medical devices to be used in the present invention include, but are not limited to, medical devices made from ceramics, metal alloys, and polymers, such as stents, and polymer tubes such as catheters. The medical devices may be coated with the same waxes and in the same manner as mentioned above.

Many factors were important in determining how to prepare examples of the present invention. The selection of materials was based on a number of chemical and physical parameters of the polymer and the fiber. Among these, the melting point ($T_m$) and degradation temperature ($T_d$) are important as they determine issues regarding material selection and processing conditions. The chemical structure of the polymers will influence the adhesion of the deposited material to the substrate fibers.

Processing conditions further involve operating furnace temperature, residence time in the furnace (which influences line speed) and powder concentrations. Physical parameters such as powder particle size (mean and distribution), density, melt viscosity, electrical conductivity, etc. are among the important ones that determine the deposition characteristics. Crystallization kinetics of the binder polymer also must be considered as it has an influence on the morphology/structure of the polymer once it is cooled down from the melt during the consolidation stage. Coating polymers and fibers were chosen for the examples considering all the factors, and are summarized with their properties in Tables 1A and 1B.

TABLE 1A

| Polymer | Producer | Particle Size | $T_M$ (° C.) | $T_D$ (° C.) |
|---|---|---|---|---|
| Polycaprolactone (TONE 767) | Union Carbide | 60 | 60 | 343 |
| Polyethylene Oxide (WSR-N-10-100-Reg) | Union Carbide | 100 | 65 | 250 |
| Polyethylene Oxide (WSR-N-80-100-NF) | Union Carbide | 100 | 65 | 250 |
| Nylon 11 (BESNO) | Elf Atochem | NT | 185 | 436 |
| Poly (vinylidene Fluoride) (KYNAR 711) | Elf Atochem | 200 | 165 | 374 |
| PVDF Copolymer (KYNARFLEX 2801) | Elf Atochem | 200 | 145 | 363 |
| Poly (ether-amide) (PEBAX 4033-SA) | Elf Atochem | NT | 160 | 232 |
| High Density Polyethylene (HDPE GHR 8110) | Hoechst-Celanese | 120 | 130 | NT |
| Hydroxypropyl cellulose (KLUCEL [EXS Pharm.]) | Hercules | 100 | 190 | 350 |

(particle size is in mesh) NT = not tested

TABLE 1B

| Fiber Type | Construction | Denier | Tenacity (g/d) | $T_M$ (° C.) | $T_D$ (° C.) |
|---|---|---|---|---|---|
| Nylon 6, 6 | Untwisted Air-Entangled 3 dpf | 630 | 8 | 255 | 442 |
| Nylon 6 | Untwisted Air-Entangled 3 dpf | 1400 | 5 | 220 | 446 |
| Polypropylene | Untwisted Air-Entangled 3 dpf | 630 | 8 | 162 | 301 |
| Teflon | Monofilament | 1200 | 5 | N/A | NT |
| Polyester (VECTRAN) | Untwisted 5 dpf | 400 | 23 | 331 | NT | dpf = denier/filament

The powder coating process is shown schematically in FIG. 1. The coating line consists of a feed spool, grounding unit, electrostatic coater, furnace/oven and take-up winder. The feed spool is mounted on a metallic post that facilitates easy unwind of the fiber during operation. The fiber is then made to pass through an eyelet that is connected to a ground source to allow for grounding of the fiber. The fiber then passes through a tensioning device made of ceramic rods that can be adjusted depending on the desired packing conditions of the powder in the fiber matrix. The fiber then passes through openings provided at each end of the coater.

A B-60 coater (available from Electrostatic Technology Incorporated, a subsidiary of Nordson Corporation, Branford, Conn.) was used to conduct the processes set forth in the examples. The coater comprises a powder feeder connected to it that feeds powder, which is held in a hopper, into the rear end of the bed. A photohelic gauge placed in the bed measures the level of powder in the bed and ensures that a constant level of powder is maintained during the coating operation. A refrigerator unit ensures the delivery of clean, moisture and oil free air into the plenum of the coater, and a powder collector provides for collection of powder that is vacuumed out of the bed during operation. The coater also comprises a fire detection device and a vortex tube to assist in the formation of the powder cloud.

The powder coated fiber exits the deposition chamber and then passes through a furnace. A suitable furnace and is made by Lindberg and Glenro. The furnace has a spilt lid that is made to open and close via air actuated arms. The fiber then moves through an eyelet onto a core spool using a Leesona rewinder. The line speed can be controlled by the Leesona rewinder and is measured using a digital tachometer.

A layer of polymer powder was fluidized in the bed, which was constructed of a plastic material. The powder was fluidized by air that was charged negatively in the plenum of the coater. The air was kept clean and free of moisture and oil by passing it through a refrigeration unit. The air was then made to pass through the air plenum and encountered a mesh of electrodes that were charged by a highly negative direct current supply.

Negative coronas used as negatively charged powder particles tend to deposit more uniformly and efficiently than positively charged ones because of their relative resistance to electric breakdown. The electrons generated in the glow region of the negative corona quickly attach themselves to electronegative gas molecules such as oxygen in the air to form negative ions. The negatively charged air then passed through a porous ceramic or plastic bed to contact the powder. Field charging or ion bombardment then transferred some of the ions to the powder particles thereby generating an aerated, negatively charged cloud of powder in the bed. This indirect charging of the powder by the air along with the separation of the charging mesh from the powder makes the fluidized bed process different from other powder techniques such as powder spray gun and triboelectric charge guns. The substrate, which in the present case was the fiber, was then grounded in order to generate a sufficient potential difference to facilitate electrostatic deposition.

The amount of polymer binder added to the fibers was the main dependent variable for the design of experiments. The powder coating variables that could have an impact on the add-on are bed fluidization flow rate ("$m^3$/sec"), electrostatic voltage (kilovolts, "kV") and line speed (meters per minute). The other variables that can be controlled on the coater are bed air pressure, vortex flow rate and vortex air pressure. It was determined that none of these latter variables influenced the add-on significantly.

The vortex tube settings were changed to create the powder cloud and once the cloud was generated, the settings were kept constant throughout the experiment. The bed agitator was turned on whenever needed, but was avoided as much as possible, as it was seen to reduce the add-on due to additional turbulence in the powder cloud. In general, wherever possible, a two parameter, three level design of experiments was conducted. The variables were varied within the following limits:

Bed fluidization flow rate ($m^3$/sec): Low (0.006); Medium (0.010); and High (0.014)

Electrostatic voltage (kV): Low (0 or no voltage); Medium (20.2); and High (40.4)

It was important to determine the furnace temperature in order to optimize the polymer fusion and bonding on the fiber. A visual experiment was carried out on nylon 6 fibers and polyethylene oxide binder. The residence time in the furnace for a line speed of 10 m/min was calculated based on the length of the furnace (approximately 1 meter) to be 6.3 seconds.

Fiber was coated at a bed flow rate of 0.014 $m^3$/sec and electrostatic voltage of 40.2 kV and was then inserted into the furnace at a selected temperature and held there for 6.3 seconds. Optical microscopy was performed to check the melt morphology of the polymer on the fibers. The furnace temperature was then raised and a freshly coated sample was exposed to the temperature. This was done until a temperature was reached at which melt occurred. It was observed that a good coating was formed on the fibers at a furnace temperature of 265° C.

The procedure described above was utilized to determine the furnace temperature for a given set of materials and process conditions. The residence time in the oven can be increased by using longer ovens or by wrapping the coated yarn in grooves of metallic rollers mounted on pulleys in the heated section of shorter ovens.

EXAMPLE 1

Polyamide Multi-Filaments/Water Soluble Polymer Coating Systems (a) Nylon 6 Multi-filaments/Poly(Ethylene Oxide)

Poly(ethylene oxide) [PEO] N-80 grade was used to coat a nylon 6 multi-filament structure comprising 467 filaments, each filament having a denier of 3. Tables 2 and 3 show the add-on (%) of PEO as a function of electrostatic voltage and bed flow rate, respectively, at an oven temperature of 260° C. and a line speed of 16 m/min. The add-on increases with increasing voltage but decreases beyond a voltage value of 40 kV. On the other hand, the trend with respect to bed flow rate indicates a strong monotonic dependence where the add-on increases with increasing flow rate. PEO powder was uniformly dispersed and fused on the nylon 6 fibers as was observed by scanning electron microscopy.

TABLE 2

| Bed Flow Rate ($m^3$/sec) | Electrostatic Voltage (KV) | Add On (%) |
| --- | --- | --- |
| 0.006 | 0 | 1.73 |
| 0.006 | 20 | 9.8 |
| 0.006 | 40.4 | 10.2 |
| 0.006 | 60.2 | 1 |
| 0.010 | 0 | 4.17 |
| 0.010 | 20 | 22.64 |
| 0.010 | 40.4 | 24.14 |
| 0.010 | 60.2 | 3.75 |
| 0.014 | 0 | 7.14 |
| 0.014 | 20 | 28.57 |
| 0.014 | 40.4 | 36.21 |
| 0.014 | 60.2 | 5 |
| 0.014 | 80.4 | 5.35 |

TABLE 3

| Electrostatic Voltage (KV) | Bed Flow Rate $m^3$/sec | Add On (%) |
| --- | --- | --- |
| 0 | 0.006 | 1.73 |
| 0 | 0.010 | 4.17 |
| 0 | 0.014 | 7.14 |
| 20.6 | 0.006 | 9.8 |
| 20.6 | 0.010 | 22.64 |
| 20.6 | 0.014 | 28.57 |
| 40.3 | 0.006 | 10.32 |
| 40.3 | 0.010 | 24.14 |
| 40.3 | 0.014 | 36.21 |
| 60.2 | 0.006 | 1 |
| 60.2 | 0.010 | 3.75 |

TABLE 3-continued

| Electrostatic Voltage (KV) | Bed Flow Rate m³/sec | Add On (%) |
|---|---|---|
| 60.2 | 0.014 | 5 |
| 80.4 | 0.014 | 5.35 |

(b) Nylon 6,6 Multi-filaments/Poly(ethylene Oxide):

PEO N-80 was used to coat a nylon 6,6 multi-filament structure comprising 210 filaments, each having a denier of 3, at a furnace temperature of 237° C. Tables 4 and 5 show the add-on of PEO as a function of voltage and flow rate at line speeds of 11 m/min and 17 m/min, respectively. As seen from the Tables, regardless of the line speed, the add-on is very sensitive to bed flow rate, with increasing flow rates resulting in higher add-on. The trend with voltage is the same as in the previous case with the existence of a saturation voltage beyond which increasing voltage results in a drop in add-on. The saturation voltage in the present case appeared to be 40 kV. The add-on also seemed to be higher at 17 m/min as compared to 11 m/min, but higher speeds did not support this trend. Scanning electron micrographs showed that PEO was uniformly coated on the nylon 6,6 fibers.

TABLE 4

| | Add-On (%) | |
|---|---|---|
| Voltage | 0.006 m³/sec | 0.014 m³/sec |
| 0 | 5.13 | 19.23 |
| 20 | 7.14 | 22.22 |
| 40 | 3.33 | 15.69 |
| 60 | 3 | 15.38 |

TABLE 5

| | Add-On (%) | |
|---|---|---|
| Voltage | 0.006 m³/sec | 0.014 m³/sec |
| 0 | 2.5 | 17.07 |
| 20 | 3.64 | 24.1 |
| 40 | 3 | 26.67 |
| 60 | 1 | 22.73 |
| 80 | 0.6 | 23 |

A study was conducted after coating nylon 6,6 with 20% PEO at an oven temperature of 235° C., voltage of 30 kV, flow rate of 0.013 m³/sec, bed pressure of 45 psi, vortex pressure of 20 psi and line speed of 11 m/min. Table 6 summarizes the results of a consumer test of PEO coated nylon 6,6 floss. The data (percent of people who indicate the floss passes each test) shows that the PEO coated floss performed well, particularly at ease of sliding between teeth and being gentle on the gums.

TABLE 6

| Property | Percent Pass |
|---|---|
| Sliding easily between teeth | 63 |
| Being gentle to the gums | 55 |
| Cleaning effectively between all teeth | 24 |

(c) Nylon 6,6 Multi-filaments/Hydroxypropyl Cellulose:

Nylon 6,6 was coated with hydroxypropyl cellulose. Tables 7 (line speed of 11 m/min, oven=235° C.) and 8 (line speed of 16 m/min, oven=255° C.) show that the add-on of hydroxypropyl cellulose ("HPC") was dependent on the bed flow rate which was the dominant factor. HPC powder possessed large amounts of charge as received from the supplier. The powder floated and tended to melt onto the fiber once deposited.

TABLE 7

| Voltage (kV) | Add-on (%) at 0.006 m³/sec | Add-on (%) at 0.014 m³/sec |
|---|---|---|
| 0 | 0 | 9.09 |
| 40 | 2 | 11.76 |
| 80 | 1.2 | 12.5 |

TABLE 8

| Voltage (kV) | Add-on (%) at 0.006 m³/sec | Add-on (%) at 0.014 m³/sec |
|---|---|---|
| 0 | 0 | 14.81 |
| 40 | 3.57 | 18.18 |
| 80 | 4 | 15 |

EXAMPLE 2

Polyester Multi-Filaments/Water Insoluble Polymer Coating Systems (a) VECTRAN Multi-filaments/High Density Polyethylene:

VECTRAN is a high performance/high temperature fiber made from liquid crystalline polyester and is commercially available from Hoechst-Celanese. A furnace temperature of 310° C. was used to melt the water-insoluble polyethylene coating material onto the VECTRAN fiber at a line speed of 17 m/min. Table 9 shows that in order to achieve higher add-ons of polyethylene, high flow and voltage was essential.

TABLE 9

| Voltage (KV) | Add On (%) |
|---|---|
| 0 | 9.35 |
| 20.2 | 8.38 |
| 40.3 | 8.1 |
| 60.1 | 14.8 |
| 80.5 | 55 |

The flow rate required to achieve the above add-ons was 0.014 m³/sec.

EXAMPLE 3

Fluoropolymer Monofilament/Water Soluble Polymer Coating Systems (a) Poly(tetrafluoroethylene) ("PTFE") Monofilament/Poly(ethylene oxide):

PTFE monofilament was coated with a non-wax water-soluble polymer, i.e., poly(ethylene oxide), to increase the coefficient of friction. The PTFE monofilament was generally rectangular in transverse cross-section, with a width of about 2–3 mm and a thickness of about 0.08–0.13 mm. The temperature was 320° C. at a line speed of 27 m/min. Table 10 shows the add-on of PEO on the PTFE monofilament tape, and it was observed that beyond 20 kV voltage the add-on drops as was seen earlier. This shows that the trend of add-on versus voltage is independent of substrate geometry, i.e., cylindrical versus flat fibers. PTFE was also successfully coated with a mixture of multiple powders such as PEO, spray-dried peppermint flavor and sodium saccharin.

TABLE 10

| Voltage (kV) | Add-On (%) | | |
|---|---|---|---|
| | 0.006 m³/sec | 0.010 m³/sec | 0.014 m³/sec |
| 0 | 10.26 | 10.22 | NT |
| 21.0 | 18.39 | 18.7 | 21.62 |
| 40.2 | 10.58 | 11.9 | NT |
| 60.2 | 7.5 | 9.1 | NT |
| 80.4 | 9.1 | 11.2 | NT |

Tables 11A and 11B summarize all the coating experiments that were conducted on different classes of fibers using different polymer coating systems and the preferred conditions for each set of materials. The main variables were bed pressure (0.006 to 0.014 m³/sec), voltage (0 to 80-kV) and line speed (6 to 64 m/min for Nylon 6/PEO N80, and 11 to 17 m/min for the rest of the materials tested). The furnace temperature was changed based on the fiber/polymer combination. If desired, further consolidation can be carried out on the powder-coated fibers in order to prepare a thoroughly impregnated product. A combination of heat and pressure can be used to drive the polymer inside the fibers that will produce a void free product. Using the viscous flow of the polymer through the fibrous network and the elastic deformation of the fiber network, a consolidation model can be developed.

TABLE 11A

| | | Preferred Conditions | | | |
|---|---|---|---|---|---|
| Fiber | Polymer | Pressure | Voltage | Speed | Comments |
| Nylon 6 | PEO N80 | 0.014 | 40.4 kV | 11 m/min | Oven = 260° C. Binder = 1.75% to 31% |
| Nylon 6, 6 | PEO N80 | 0.014 | 20.2 kV | 11 m/min | Oven = 237° C. Binder = 1.5% to 27% Reduced add on due to turbulence |
| | PEG 8000 | | | | Larger particle size, High density/poor floatation, Low molecular weight, good melt |
| | Klucel | 0.014 | 40.2 kV | 17 m/min | Powder was very fine, Extremely cohesive, Agitator had to be used, Feed hopper could not be used |

TABLE 11B

| | | Preferred Conditions | | | |
|---|---|---|---|---|---|
| Fiber | Polymer | Pressure | Voltage | Speed | Comments |
| Nylon 6, 6 | KYNAR 711 KYNAR-FLEX PCL | | | | KYNAR powders - high densities, fine particle size, PCL did not charge due to its size, grinding down was not possible |
| Polypropylene | PEO N80 | 0.010 | 20.2 kV | 11 m/min | Fiber performed very well, low melting point made coating difficult |
| VECTRAN | HDPE | 0.014 | 80.2 kV | 17 m/min | Powder was extremely heavy, oven = 310° C. |
| Teflon | HDPE | 0.014 | 80.2 kV | 17 m/min | Powder was extremely heavy, oven = 310° C., good melt but poor adhesion |
| | PEO N80, flavor, saccharin | 0.006 | 20.2 kV | 27 m/min | Excellent floatation, oven = 320° C., increased blend ratio |

EXAMPLE 4

Selection Process for Polymer Powders Based on Powder Aeration

It is necessary to understand powder aeration to predict the coating performance of polymer powders. In order to understand this quantitatively, experiments were carried out on several powders to obtain their bulk and tapped densities. In this experiment, a clean graduated cylinder was taken and weighed ($W_1$). 50 cc. of powder was then poured into the cylinder and weighed again ($W_2$). Weights were recorded to 5 decimal precision. The aerated/bulk density was then computed using equation (1).

$$\rho_b = \frac{W_2 - W_1}{50}, \quad (1)$$

where $\rho_b$ is the bulk density in grams/cc.

In order to obtain the tapped density the same measurements were made with a minor difference. After the powder was poured into the cylinder, it was tapped 50 times in order to compact it and powder was added to maintain a 50 ml volume. The cylinder was then weighed ($W_3$). Equation 1 was used after substituting $W_3$ for $W_2$, and the tapped density was obtained in grams/cc. Table 12 lists the bulk and tapped densities of the different polymers. The fused density in the table represents the density of a block of material.

TABLE 12

| Polymer | Bulk Density (g/cc) | Tapped Density (g/cc) | Fused Density (g/cc) |
|---|---|---|---|
| Polyethylene Oxide WSR-N-10-100-Reg WSR-N-80-100-NF | 0.46–0.50 | 0.54 | 1.2 |
| Polycaprolactone 767 | 0.52 | 0.61 | 1.15 |
| Polyethylene Glycol | 0.54 | 0.82 | 1.03 |
| Polyethylene GHR 8110 | 0.47 | 0.51 | 0.95 |
| HPC (Klucel) | 0.32 | 0.39 | 1.16 |

The differential densities (fused density–tapped density) of the polymer particles were plotted (log-log) as a function of mean particle size (in microns). It appears that the relationship of these polymer properties is critical to the polymer's fluidization properties, such as aeratability, cohesiveness, sand-like properties, and spoutability. The data can be used as a guide in selecting powders for fluidized-bed coating applications. For example, PEO and HPC are more aeratable than Polyethylene glycol and Polyethylene GHR 8110 (a high density polyethylene). Therefore, PEO and HPC are more easily fluidized.

I claim:

1. A process comprising:
    providing a fiber substrate selected from the group consisting of a monofilament fiber and multi-filament fibers; electrically grounding the fiber substrate; in a coater bed, fluidizing a powder coating material in air that is negatively charged in a plenum of a coater; passing the fiber substrate through the coater bed to coat the fiber substrate with the coating material; and heating the coating material to melt the coating material onto the fiber substrate to generate a coated fiber substrate that is useful as a dental floss.

2. The process of claim 1, wherein the fiber comprises a material selected from the group consisting cellulosics; polyamides; polyesters; polyolefins; poly(ether-amides); poly(ether-esters); fluorinated polymers; copolymers thereof; and blends thereof.

3. The process of claim 2, wherein the polyamide is selected from the group consisting of nylon 6, nylon 11, nylon 12, and nylon 6,6;
    the polyester is selected from the group consisting of polycaprolactone; poly(ethelene terephthalate); and poly(butylene terephthalate);
    the polyolefin is selected from the group consisting of polypropylene and polyethylene; and
    the fluorinated polymer is poly(vinylidene fluoride).

4. The process of claim 3, wherein the coating is selected form the group consisting of poly(ethylene oxide), poly(ethylene glycol), hydroxyethyl cellulose, hydroxypropyl cellulose, polyethylene, wax, elastomers, polycaprolactone and combinations thereof.

5. The process of claim 4, wherein a second coating is electrostatically applied to the substrate.

6. The process of claim 5, wherein the second coating is selected from the group consisting of poly(ethylene oxide), poly(ethylene glycol), hydroxyethyl cellulose, hydroxypropyl cellulose, polyethylene, wax, elastomers, polycaprolactone and combinations thereof.

* * * * *